United States Patent [19]

Pierce

[11] Patent Number: 5,442,115
[45] Date of Patent: Aug. 15, 1995

[54] PREPARATION OF ALPHA-CHLOROACETOACETANILIDE COMPOUNDS

[75] Inventor: Benjamin J. Pierce, Southbury, Conn.

[73] Assignee: Uniroyal Chemical Company, Inc., Middlebury, Conn.

[21] Appl. No.: 260,147

[22] Filed: Jun. 15, 1994

[51] Int. Cl.$^6$ .......................................... C07C 225/22
[52] U.S. Cl. .................................................. 564/200
[58] Field of Search ................. 560/174, 178; 564/200

[56] References Cited

U.S. PATENT DOCUMENTS 3,459,801  8/1969  Beriger ................................ 564/200
5,049,698  9/1991  Newland ............................ 564/200

Primary Examiner—James H. Reamer
Attorney, Agent, or Firm—Daniel Reitenbach

[57] ABSTRACT

A process for the preparation of α-chloroacetoacetanilide compounds (α-Cl AAA) which comprises the steps of:

(a) reacting an acetoacetanilide compound (AAA) with chlorine in the presence of a solvent mixture consisting essentially of an organic solvent and water, wherein the percent water to organic solvent in the solvent mixture is between about 10% and 150% (v/v);

(b) isolating the α-Cl AAA produced in step (a); and (c) optionally hydrogenating any α,α-dichloroacetoacetanilide compound (α,α-diCl AAA) produced in step (a), with hydrogen in the presence of a catalyst selected from the group consisting of palladium, platinum and Raney nickel, and in the presence of a solvent mixture consisting essentially of water and an organic solvent, wherein the percent of the water to the organic solvent in the solvent mixture is between 10% to 150% (v/v), for a period of time sufficient to produce α-Cl AAA; and isolating the α-Cl AAA so produced.

The present invention also relates to a process for the dechlorination of α,α-diCl AAA wherein the α,α-diCl AAA is hydrogenated with hydrogen in the presence a catalyst selected from the group consisting of palladium, platinum and Raney nickel, and in the presence of a solvent mixture consisting essentially of water and an organic solvent, wherein the percent of the water to the organic solvent in the solvent mixture is between 10% to 150% (v/v), for a period of time sufficient to produce either α-Cl AAA or AAA.

20 Claims, No Drawings

PREPARATION OF ALPHA-CHLOROACETOACETANILIDE COMPOUNDS

FIELD OF THE INVENTION

This invention relates to an improved process for producing α-chloroacetoacetanilide compounds by chlorination of acetoacetanilide compounds. More particularly, this invention relates to an improved process for producing α-chloroacetoacetanilide compounds by chlorination of acetoacetanilide compounds using a solvent mixture of water and an organic solvent.

This invention also relates to an improved process for producing α-chloroacetoacetanilide compounds by dechlorination of α,α-dichloroacetoacetanilide compounds.

BACKGROUND OF THE INVENTION

α-chloroacetoacetanilide is an important intermediate in the preparation of carboxin which is an agent used to control numerous plant diseases. See, e.g., U.S. Pat. No. 3,249,499.

The chlorination of acetoacetanilide compounds with chlorine to produce α-chloroacetoacetanilide compounds is cheaper than using other chlorinating agents such as sulfuryl chloride but has the disadvantage of being non-selective and giving large quantities of by-product α,α-dichloroacetoacetanilide compounds and unreacted acetoacetanilide compounds.

Attempts to overcome this problem have been described. For example, U.S. Pat. No. 3,852,351 describes the reaction of acetoacetamides with chlorine to form the corresponding α-chloro compound. The reaction takes place in a substantially anhydrous reaction medium consisting of a polar solvent and a compound which causes enolization, such as a Lewis acid or chelates.

Czechoslavakian Patent Document 170709 describes a method for synthesizing α-chloroacetoacetanilide by chlorinating acetoacetanilide with elemental chloride in a medium consisting of an organic solvent (methanol or tetrachloromethane) or a mixture of such an organic solvent with hydrochloric acid or glacial acetic acid.

SUMMARY OF THE INVENTION

The present invention relates to a process for the preparation of an α-chloroacetoacetanilide compound (α-Cl AAA) of the formula

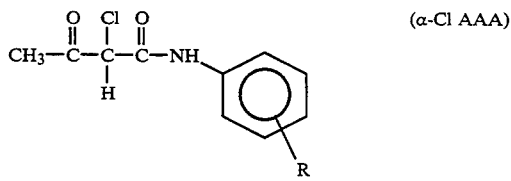

wherein R is hydrogen, halogen or $C_1$-$C_4$ alkyl, preferably, hydrogen, chlorine, methyl or ethyl, which comprises the steps of:

(a) reacting an acetoacetanilide compound (AAA) of the formula

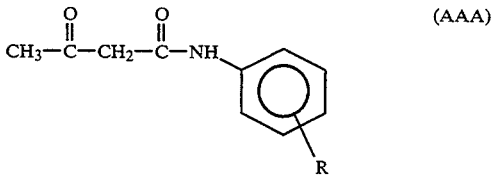

wherein R is as described above, with chlorine in the presence of a solvent mixture consisting essentially of an organic solvent and water, wherein the percent water to organic solvent in the solvent mixture is between about 10% and 150% (volume to volume, "v/v"), preferably between about 20% and 100% (v/v);

(b) isolating the α-Cl AAA produced in step (a); and
(c) optionally hydrogenating any α,α-dichloroacetoacetanilide compound (α,α-diCl AAA) of the formula

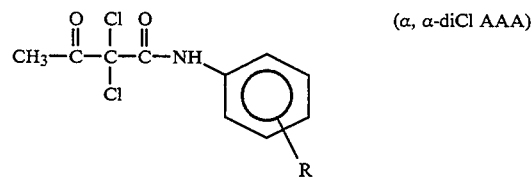

wherein R is as defined above, produced in step (a), with hydrogen in the presence of a catalyst selected from the group consisting of palladium, platinum, rhodium, and Raney nickel, in the form of a bulk metal or oxide, preferably supported on a suitable carrier such as carbon or aluminum, and in the presence of a solvent mixture consisting essentially of water and D-6150 an organic solvent, wherein the percent of the water to the organic solvent in the solvent mixture is between 10% to 150% (v/v), for a period of time sufficient to produce α-Cl AAA; and isolating the α-Cl AAA so produced.

The present invention also relates to a process for the dechlorination of α,α-diCl AAA wherein the α,α-diCl AAA is hydrogenated with hydrogen in the presence a catalyst selected from the group consisting of palladium, platinum, rhodium and Raney nickel, in the form of a bulk metal or metal oxide, preferably supported on a suitable carrier such as carbon or aluminum, and in the presence of a solvent mixture consisting essentially of water and an organic solvent, wherein the percent of the water to the organic solvent in the solvent mixture is between 10% to 150% (v/v), for a period of time sufficient to produce either α-Cl AAA or AAA. More preferably, the catalyst is selected from the group consisting of palladium on carbon, platinum on carbon, rhodium on carbon, and platinum oxide. Particularly preferred is palladium on carbon.

DETAILED DESCRIPTION OF THE INVENTION

When AAA is chlorinated by chlorine gas in solution, the product is generally a mixture of α-Cl AAA, α,α-diCl AAA and unreacted AAA starting material.

The solvent mixture useful in the process of the present invention is a mixture of water and an organic solvent. The organic solvent can be either miscible or immiscible with water, and includes, for example, toluene, xylene, dioxane, isopropyl alcohol, ethanol, 1,2-dichloroethane, chloroform, carbon tetrachloride and chlorobenzene, with toluene being preferred. The percent of the water to the organic solvent in the solvent mixture, is at least about 10% (v/v), i.e., for every 100 ml of organic solvent in the solvent mixture, there should be at least about 10 ml of water. The chlorination reaction can be conducted in the presence of a solvent mixture in which the percent of water to organic solvent in the solvent mixture can be as high as 150% (v/v), i.e., for every 100 ml of organic solvent there can be as much as about 150 ml of water, although yields of α-Cl AAA level off after the percent of water to organic solvent in the solvent mixture exceeds 20% (v/v). The reaction can be conducted at a temperature of about 0° C. to about 20° C., preferably at a temperature of about 0° C. to 10° C.

For best results, it is preferable to use a slight molar excess of chlorine gas based on moles of AAA starting material. For example, using a solvent mixture of 80 ml toluene/15 ml water at 8° C. and 0.1 moles of acetoacetanilide starting material, the yield of α-chloroacetoacetanilide peaked at 0.11 moles of chlorine gas added. At higher amounts of chlorine gas, yields of α-chloroacetoacetanilide decreased while yields of α,α-dichloroacetoacetanilide increased. Flow rate of chlorine gas also affects product yield, with yields of α-Cl AAA generally increasing with flow rate up to a point depending on the other reaction variables, then decreasing thereafter. For example, using a solvent mixture of 80 ml toluene/15 ml water at 8°–10° C. and 0.1 moles of starting material, yield of the α-chloroacetoacetanilide peaked at a flow rate of 0.19 grams per minute.

Also having an effect on the reaction is the particle size of the AAA starting material when small amounts of the organic solvent are used in the solvent mixture. For example, when using 0.1 moles of AAA in 80 ml of toluene (approximately 22% (w/v) acetoacetanilide in toluene), yield of α-chloroacetoacetanilide increased with particle size of the acetoacetanilide used. However, when 0.3 moles of acetoacetanilide in 433 ml of toluene (approximately 12% (w/v) acetoacetanilide in toluene) was used, particle size of the acetoacetanilide had no effect on the yield of α-chloroacetoacetanilide. 10–15% AAA (w/v) in toluene is preferred.

In general, the yield of α-Cl AAA increases with increasing volume of solvent mixture.

Since the chlorination process generally results in formation of undesired α,α-diCl AAA as a by-product, another aspect of this invention is an improved method for dechlorinating α,α-diCl AAA to produce α-Cl AAA, thereby increasing the overall yield of α-Cl AAA. Using this method, α,α-diCl AAA is reacted with hydrogen in the presence of a catalytic amount of a suitable catalyst selected from the group consisting of palladium, platinum and Raney nickel, in the form of a bulk metal, metal chloride or metal oxide. Preferably such catalyst is supported on a suitable carrier such as carbon or aluminum. More preferably, the catalyst is selected from the group consisting of palladium chloride, palladium on carbon, platinum on carbon and platinum oxide. Such catalysts are typically employed in amounts of about 0.5% to about 10% (w/w) of α,α-diCl AAA. A particularly preferred catalyst is 5% palladium on carbon (Pd/C), preferably at a catalyst level of about 0.5% to 10% (w/w), more preferably about 2% to 4% (w/w), of the α,α-diCl AAA present. The α,α-diCl AAA is dissolved in the solvent mixture described above for chlorinating AAA. Particularly preferred is a solvent mixture of 10% (v/v) water in toluene. The hydrogenation reaction is generally conducted at a temperature of between 20° C. and 100° C., preferably between 20° C. and 80° C.

The hydrogenation reaction generally takes place in two distinct phases. In the first phase, hydrogen is taken up rapidly with time, then after a point, the uptake is more gradual. It is believed that during this rapid uptake, the dominant reaction is the conversion of α,α-diCl AAA to α-Cl AAA. During the second phase, there is less rapid uptake of hydrogen and it is believed that the primary reaction is the conversion of α-Cl AAA to AAA. It is, therefore, believed to be advantageous to stop the reaction by removing the hydrogen atmosphere when the uptake of hydrogen changes from rapid to slower, thereby insuring maximum recovery of the α-Cl AAA. Uptake of hydrogen in the hydrogenation reaction can be determined using a gauge to measure the pressure drop or by the use of a hydrogen burette.

EXAMPLES

The following examples are provided to illustrate the present invention.

Example 1

Chlorination of Acetoacetanilide in Toluene/Water with Chlorine

Acetoacetanilide (17.7 g, 0.10 mole) was suspended in a mixture of toluene and water (40 ml each) and the mixture was cooled in an ice bath. Chlorine gas (7.1 g, 0010 mole) was bubbled into the mixture slowly over about 15 minutes. After stirring an additional 15 minutes, the solid smelling strongly of HCl was filtered off and dried in a vacuum oven. The filtered solid weighed 19.0 g and NMR analysis showed 20.4% acetoacetanilide, 73.2% α-chloro-acetoacetanilide, and 6.4% α,α-dichloroacetoacetanilide.

The residue from the filtrate weighed 1.9 g and NMR analysis showed 4.4% acetoacetanilide, 11.0% α-chloroacetoacetanilide, and 84.6% α,α-dichloroacetoacetanilide.

Combining these figures the overall composition of the product was: α-chloroacetoacetanilide 67.0%; α,α-dichloroacetoacetanilide 11.5%; acetoacetanilide 22.5%.

Comparative Example A

Chlorination of Acetoacetanilide in Toluene with Chlorine

Acetoacetanilide (17.7 g, 0.10 mole) was suspended in toluene (40 ml) and the mixture was cooled in an ice bath, and chlorine gas (7.1 g, 0.10 mole) was bubbled into the mixture slowly over about 15 minutes. After stirring an additional 15 minutes, the solid smelling strongly of HCl was filtered off and dried in a vacuum oven. 7.3 g of solid was obtained which NMR analysis showed to be 18% α-chloroacetoacetanilide and 82% acetoacetanilide.

The toluene was removed from the filtrate to leave 12.2% α-chloroacetoacetanilide and 8.4% acetoacetanilide.

The overall yield of the various components calculated from the above weights and percentage compositions was: α-chloroacetoacetanilide 15.2%; α,α-dichloroacetoacetanilide 37.4%; acetoacetanilide 40.0%.

Example 1 and Comparative Example A demonstrate that the yield of the desired α-chloroacetoacetanilide unexpectedly increased dramatically when the solvent mixture of the process of the present invention is used, compared to the use of an anhydrous solvent.

Example 2

Dehalogenation of α,α-dichloroacetoacetanilide in Toluene/Water

An atmospheric pressure hydrogenation apparatus was used. This apparatus consisted of a calibrated burette to contain the hydrogen and conical flask whose contents were stirred magnetically to contain the reaction mixture.

A mixture consisting of 50 ml of water and 12.3 g (0.05 mole) of α,α-dichloroacetoacetanilide [prepared by the method of C. Bulow and E. King, Ann 439,211 (1924)] dissolved in 50 ml toluene was placed in the conical flask and then 0.25 g of 5% Pd/C was added. The burette was filled with hydrogen and the stirrer started. Hydrogen uptake began immediately and could be followed with time. When 0.05 mole (1255 ml at 25° C. and 740 mm pressure) of hydrogen had been absorbed the reaction was stopped. The mixture was heated on the steam bath and filtered while hot to remove the catalyst. Solid separated immediately from the filtrate as it cooled. This solid, 4.35 g, was filtered off, mp 126°–130° C. An infrared spectrum of this material was identical to the spectrum of α-chloroacetoacetanilide. The water phase of the filtrate was separated off and the toluene removed from the organic phase to leave 6.15 grams of a crystalline residue of less pure α-chloroacetoacetanilide, mp 110°–120° C. This was purified by slurrying it in 30 ml of toluene and filtering off 4.95 g, mp 125°–132° C. The total yield of α-chloroacetoacetanilide was 9.3 g or 89%.

Example 3

This experiment was carried out to demonstrate the full course of hydrogenation through α-chloroacetoacetanilide to acetoacetanilide using the same atmospheric pressure hydrogenation apparatus as in Example 2 above.

2.46 g (0.01 mole) of α,α-dichloroacetoacetanilide was dissolved in 20 ml of water and 30 ml of toluene, and dehalogenated with hydrogen using 5% Pd/C as catalyst. Hydrogen was allowed to react until no more would be absorbed. The first equivalent (251 ml at 739 mm pressure and 25° C.) was absorbed in 50 minutes (a rate of about 5 ml/min) whereas the 274 ml (second equivalent) was absorbed at the much slower rate of about 0.9 ml/min. On the basis of the hydrogen absorbed, it was concluded that the dehalogenation had proceeded to remove both chlorines and hence to give acetoacetanilide. This was confirmed by filtering off the catalyst, separating off the water phase and finally isolating the product from the toluene. Obtained were 1.57 g or 89% of acetoacetanilide, mp 79°–84° C.

Example 4

Using the atmospheric pressure hydrogenation apparatus described above in Example 2, 0.05 g of 5% Pd/C was added to a mixture of 2.46 g (0.01 mole) of α,α-dichloroacetoacetanilide, 90 ml of toluene and 10 ml of water. The mixture was stirred under a hydrogen atmosphere. The first 190 ml (0.01 mole) of hydrogen (α,α-dichloroacetoacetanilide→acetoacetanilide) was taken up at the rate of about 0.2 ml/minute. The reaction was stopped after 130 minutes when 319 ml (0.017 mole) of hydrogen had been absorbed (70% complete to acetoacetanilide) and the product was isolated by filtering off the catalyst and removing the toluene from the filtrate. NMR analysis showed 11.6% acetoacetanilide, 88.4% α-chloroacetoacetanilide, and 0.0% α,α-dichloroacetoacetanilide.

This example indicates that all the α,α-dichloroacetoacetanilide was reduced to α-chloroacetoacetanilide before α-chloroacetoacetanilide was reduced to acetoacetanilide, i.e., under the conditions used the reaction was selective.

Comparative Example B

Dehalogenation of α,α-Dichloroacetoacetanilide in Toluene

Using the atmospheric pressure hydrogenation apparatus described above in Example 2, a mixture of 2.46 g (0.01 mole) of α,α-dichloro-acetoacetanilide, 100 ml of toluene, and 0.05 g of 5% Pd/C was stirred under 1 atm of hydrogen. After 125 minutes, 246 ml of hydrogen had been taken up, but this number was probably depressed because the HCl formed was not very soluble in toluene and would, therefore, have reduced the reading. The catalyst was filtered from the toluene and the solvent removed to leave 2.18 g of residue which NMR analysis showed to be: acetoacetanilide 18.3%; α-chloroaceto-acetanilide 59%; and α,α-dichloroacetoacetanilide 21.8%. Comparison of this result with the result of the identical experiment done in toluene with 10% water (Example 4) shows that water has an unexpected beneficial effect on the selectivity of the dehalogenation.

Example 5

A Cyclic Process for Producing α-Chloroacetoacetanilide

This experiment describes a cyclic process for producing α-chloroacetoacetanilide.

A suspension of 177 g (1.0 mole) of acetoacetanilide in 1440 ml of toluene and 167 ml of water, in a chlorinator (2000 ml 3-neck flask), was cooled to approximately 6° C. and chlorine gas was added at about the rate of 1.5 g/minute, while maintaining the temperature at 6° C. until 82.6 g (1.16 moles) of chlorine had been added (about 56 minutes). The resultant mixture was stirred for an additional 36 minutes and then heated to 70° C. for 15 minutes. The mixture was then cooled and the product was precipitated. The precipitate was filtered from the toluene/aqueous HCl mixture to give 134.8 g (63.9%) of α-chloroacetoacetanilide, mp 132°–134° C.

The aqueous HCl phase was separated from the toluene/aqueous HCl filtrate and 170 ml of distilled water was added to the remaining toluene phase along with 1.0 g of 5% Pd/C. The mixture was hydrogenated under one atmosphere of hydrogen. The initial rate of uptake was about 79 ml/minute, and the hydrogenation was stopped when this uptake had fallen to about 19 ml/minute. The catalyst was filtered off and the toluene/H$_2$O filtrate was returned to the chlorinator. A small sample (4 ml) of the toluene phase was removed and the toluene evaporated. The residue (0.1991 g) was analyzed by NMR as containing acetoacetanilide, 34.7%; α-chloroacetoacetanilide, 65.3%; and α,α-dichloroacetoacetanilide 0.0%. Since the total toluene phase was 1462 ml the weight of each component in this phase could be calculated as acetoacetanilide, 24.2g; α-chloroacetoacetanilide, 45.5g and α,α-dichloroacetoacetanilide 0.0 g. The acetoacetanilide content of the chlorinator was then made up to 1 mole (177 g) by the addition 152.8 g of fresh acetoacetanilide, and the chlorination was repeated once more followed by isolation of the α-chloroacetoacetanilide (150.8 g, mp 131°–134° C.). The cycle was repeated four times. The results of these cycles is shown in Tables I and II.

After 4 cycles 630.3 g. of acetoacetanilide had been converted into 614.3 g or 81.8% of pure (>97%) α-chloroacetoacetanilide. The hydrogenate after the 4th cycle contained 68.5 g of additional α-chloroacetoacetanilide which was not isolated, but if taken into account would potentially have given 682.8 g or 90.9% of α-chloroacetoacetanilide.

2. A method as recited in claim 1 wherein R is hydrogen, chlorine, methyl or ethyl.

3. A method as recited in claim 2 wherein R is hydrogen.

4. A method as recited in claim 1 wherein the organic solvent is toluene.

5. A method as recited in claim 1 wherein the percent of the water to the organic solvent in the solvent mixture, is between about 20% and 100% (v/v).

6. A method as recited in claim 1 further comprising the steps of:

TABLE I

| | | Pure | | | Analysis of hydrogenate | | |
| --- | --- | --- | --- | --- | --- | --- | --- |
| Cycle # | Acetoacetanilide added (g) | α-chloroaceto-acetanilide obtained (g) | $H_2$ used (ml) | Catalyst used (g) | Acetoacetanilide (g) | α-chloroaceto-acetanilide (g) | α,α-dichloroaceto-acetanilide (g) |
| 1 | 177 | 134.8 | 4500 | 1.0 | 24.2 | 45.5 | 0.0 |
| 2 | 152.8 | 150.8 | 7000 | 1.0 | 27.0 | 61.0 | 0.0 |
| 3 | 150.0 | 159.8 | 7500 | 1.0 | 26.5 | 64.9 | 0.0 |
| 4 | 150.5 | 168.0 | 6500 | 1.0 | 23.7 | 68.5 | 0.0 |

TABLE II

| Cycle # | Acetoacetanilide added (g) | Cumulative wt. of acetoacetanilide added (g) | Pure α-chloro-acetoacetanilide produced (g) | Cumulative wt. of α-chloroaceto-acetanilide produced (g) | % Conversion on this cycle | Cumulative conversion |
| --- | --- | --- | --- | --- | --- | --- |
| 1 | 177 | 177 | 134.8 | 134.8 | 63.9 | 63.9 |
| 2 | 152.8 | 329.8 | 150.8 | 285.6 | 82.8 | 72.7 |
| 3 | 150.0 | 479.8 | 159.9 | 445.5 | 89.4 | 77.9 |
| 4 | 150.5 | 630.3 | 168.8 | 614.3 | 94.1 | 81.8 |

What is claimed is:

1. A method for producing an α-chloro-acetoacetanilide compound (α-Cl AAA) of the formula

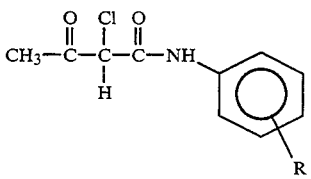

wherein R is hydrogen, halogen or $C_1$–$C_4$ alkyl, which comprises the steps of:

(a) reacting an acetoacetanilide compound (AAA) of the formula

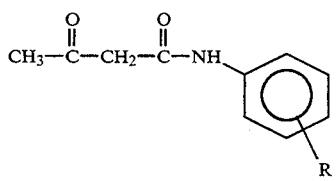

wherein R is as defined above, with chlorine in the presence of a solvent mixture consisting essentially of water and an organic solvent selected from the group consisting of toluene, xylene, dioxane, isopropyl alcohol, ethanol, 1,2-dichloroethane, chloroform, carbon tetrachloride and chlorobenzene, at a temperature of about 0° C. to about 20° C., wherein the percent of the water to the organic solvent in the solvent mixture, is between about 10% and 150% (v/v); and (b) isolating the α-Cl AAA produced in step (a).

(c) hydrogenating any α,α-dichloroacetoacetanilide compound (α,α-diCl AAA) of the formula

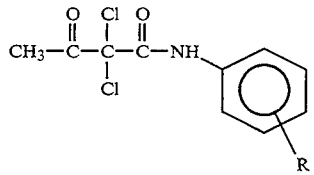

wherein R is as defined in claim 1, produced in step (a), with hydrogen in the presence of a catalyst selected from the group consisting of palladium, platinum, and Raney nickel, and in the presence of a solvent mixture consisting essentially of water and an organic solvent selected from the group consisting of toluene, xylene, dioxane, isopropyl alcohol, ethanol, 1,2-dichloroethane, chloroform, carbon tetrachloride and chlorobenzene, at a temperature of between 20° C. and 100° .C., wherein the percent of the water to the organic solvent in the solvent mixture is between 10% to 150% (v/v), for a period of time sufficient to produce α-Cl AAA; and (d) isolating the α-Cl AAA produced in step (c).

7. A method as recited in claim 6 wherein the organic solvent used in step (c) is toluene.

8. A method as recited in claim 6 wherein the catalyst is selected from the group consisting of palladium chloride, palladium on carbon, platinum on carbon and platinum oxide.

9. A method as recited in claim 8 wherein the catalyst is palladium on carbon.

10. A method for dehalogenating an α,α-dichloroacetoacetanilide compound (α,α-diCl AAA) of the formula

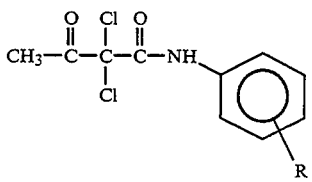

wherein R is hydrogen, halogen or $C_1$–$C_4$ alkyl, which comprises hydrogenating the α,α-diCl AAA with hydrogen in the presence of a catalyst selected from the group consisting of palladium, platinum and Raney nickel, and in the presence of a solvent mixture consisting essentially of water and an organic solvent selected from the group consisting of toluene, xylene, dioxane, isopropyl alcohol, ethanol, 1,2-dichloroethane, chloroform, carbon tetrachloride and chlorobenzene, at a temperature of between 20° C. and 100° C., wherein the percent of the water to the organic solvent in the solvent mixture is between 10% to 150% (v/v).

11. A method as recited in claim 10 wherein the organic solvent is toluene.

12. A method as recited in claim 10 wherein the catalyst is selected from palladium chloride, palladium on carbon, platinum on carbon and platinum oxide.

13. A method as recited in claim 12 wherein the catalyst is palladium on carbon.

14. In a method for the production of α-chloroacetoacetanilide by chlorination of acetoacetanilide, wherein the improvement comprises carrying out the reaction with chlorine in a solvent mixture consisting essentially of water and an organic solvent selected from the group consisting of toluene, xylene, dioxane, isopropyl alcohol, ethanol, 1,2-dichloroethane, chloroform, carbon tetrachloride and chlorobenzene, at a temperature of between 0° C. and 20° C., wherein the percentage of the volume of water to the volume of the organic solvent is between about 10% and 150%.

15. A method as recited in claim 14 wherein the organic solvent is toluene.

16. A method as recited in claim 15 wherein the percent of the water to the organic solvent in the solvent mixture is between 20% to 100% (v/v).

17. In a method for dechlorinating α,α-dichloroacetoacetanilide to form α-chloroacetoacetanilide in a hydrogenation reaction, wherein the improvement comprises carrying out the hydrogenation in the presence of a catalyst selected from the group consisting of palladium, platinum and Raney nickel, and in the presence of a solvent mixture consisting essentially of water and an organic solvent selected from the group consisting of toluene, xylene, dioxane, isopropyl alcohol, ethanol, 1,2-dichloroethane, chloroform, carbon tetrachloride and .chlorobenzene, at a temperature of between 20° C. and 100° C., wherein the percent of the water to the organic solvent in the solvent mixture is between 10% to 150% (v/v).

18. A method as recited in claim 17 wherein the organic solvent is toluene.

19. A method as recited in claim 18 wherein the catalyst is selected from palladium chloride, palladium on carbon, platinum on carbon and platinum oxide.

20. A method as recited in claim 19 wherein the catalyst is palladium on carbon.

* * * * *